(12) United States Patent
Cole

(10) Patent No.: US 6,489,170 B1
(45) Date of Patent: Dec. 3, 2002

(54) CHEMICAL SPOT TEST FOR LEAD IN PAINT AND OTHER MEDIA

(76) Inventor: Sandra Lynn Cole, 5545 Vickery Blvd., Dallas, TX (US) 75206

(*) Notice: Subject to any disclaimer, the term of this patent is extended or adjusted under 35 U.S.C. 154(b) by 0 days.

(21) Appl. No.: 09/336,614

(22) Filed: Jun. 18, 1999

Related U.S. Application Data
(60) Provisional application No. 60/110,810, filed on Dec. 3, 1998.

(51) Int. Cl.[7] .................................... G01N 33/20
(52) U.S. Cl. ................................ 436/77; 436/73
(58) Field of Search ........................ 436/77, 73

(56) References Cited

U.S. PATENT DOCUMENTS

| | | | |
|---|---|---|---|
| 3,809,537 A | * 5/1974 | Horine | 436/77 X |
| 4,873,197 A | * 10/1989 | Gould | 436/77 |
| 5,010,020 A | 4/1991 | Gould | |
| 5,039,618 A | 8/1991 | Stone | |
| 5,278,075 A | * 1/1994 | Stone | 436/73 |
| 5,330,917 A | 7/1994 | Stone | |
| 5,364,792 A | * 11/1994 | Stone | 436/73 |
| 5,416,028 A | 5/1995 | Stone | |
| 5,445,965 A | * 8/1995 | Stone | 436/81 |
| 5,492,835 A | * 2/1996 | Koenig | 436/77 |
| 5,558,835 A | * 9/1996 | Kozarsky et al. | 422/56 |
| 5,567,619 A | * 10/1996 | Stone | 436/77 |
| 6,248,593 B1 | * 6/2001 | Esswein et al. | 436/77 |

* cited by examiner

*Primary Examiner*—Jill Warden
*Assistant Examiner*—Monique T. Cole
(74) *Attorney, Agent, or Firm*—Colin P. Cahoon; Carstens, Yee & Cahoon, L.L.P.

(57) ABSTRACT

A one-step chemical spot test for the qualitative determination of lead in lead-based paint and other media. This test is based upon the reaction of lead with sodium rhodizonate under strong acid conditions to develop an intense purple colored complex. The acid preferred is dilute hydrochloric acid. The test is performed in one step using a dropper, plastic cylinders, or like apparatus.

18 Claims, 1 Drawing Sheet

CHEMICAL SPOT TEST FOR LEAD IN PAINT AND OTHER MEDIA

CROSS-REFERENCE TO RELATED APPLICATION

This application is the non-provisional submission of a provisional application of the same title filed on Dec. 3, 1998 and assigned application Ser. No. 60/110,810.

BACKGROUND OF THE INVENTION

1. Technical Field

The present invention relates to a method and apparatus for qualitatively determining the presence of lead in lead-based paint and other media while avoiding barium or other interferences by use of sodium rhodizonate and a strong acid.

2. Description of Related Art

For hundreds of years, people have used lead for different purposes. Lead was used by the Romans for soldering pipes, by others in crystal glassware, and currently in paint mixtures, as well as other applications. The hazards of lead poisoning have been known, but only in relatively recent times has the extent of the threat to children moved to the forefront. The ingestion of lead is harmful to people of all ages, but is more damaging to children under six, and unborn fetuses. The developing nervous system is more susceptible to the toxic effects of the lead. Children who have been exposed to lead exhibit behavioral and cognitive impairment at low levels, with higher levels resulting in anemia, brain damage and other irreversible effects. The risk of lead poisoning to children from lead-based paint was identified as early as 1897.

Children are exposed to lead in lead-based paint through normal childhood behaviors, such as sucking and chewing on painted surfaces, and ingesting paint chips from damaged areas. If lead-based paint is removed without appropriate precautions, the airborne particles permeate the area, and can be ingested or inhaled by both children and adults.

It is believed that ninety percent of houses built before 1940 contain lead paint. In houses built before 1950, paints used in housing contained as much as 50% lead by dry weight. After the 1940s, the use of lead-based paint decreased in residential homes.

It is estimated that more than 70% of homes built before 1980 have lead in paint and fixtures. It was commonly used in areas where durability was desired, such as trim, cabinets and outdoor areas.

In 1972 the Consumer Products Safety Commission made the first effort to regulate the lead content in paint. The Commission established a maximum lead content in paint at 0.5% lead w/w in residential paint. This limit was considered to be "safe". In 1977, lead was even further restricted from use in residential paints due to the risk of lead poisoning in children. Any lead content below 0.06% was considered as "lead-free" paint. Any paint with a lead content greater than 0.06% was still considered to be lead-based paint.

In 1990, the U.S. Department of Housing and Urban Development ("HUD") published "Lead-Based Paint: Interim Guidelines for the Identification and Abatement of Lead- Based Paint in Public and Indian Housing." The HUD guidelines described technical protocols, practices and procedures for testing, abatement, and worker protection in cleanup and disposal of lead-based paint. The HUD guidelines also required inspection of public and Indian housing before 1994, and abatement if the amounts exceeded an action level of 0.5% lead w/w, or 1 $mg/cm^2$ mass/area concentration.

Although there are no federal requirements to abate lead in private housing, in 1992 the Residential Lead-Based Hazard Reduction Act, Title X, was passed, to become effective in 1995. Title X established new requirements for homeowners and Federal agencies, and new actions to improve the safety and effectiveness of lead-based paint identification and remediation activities. This act requires the sellers of homes to disclose the existence of any lead-based paint or hazard in pre-1978 homes, and allow purchasers 10 days to inspect before becoming obligated to purchase the house.

In response to requirements made by Title X, HUD issued new guidelines, entitled "The Guidelines for the Evaluation and Control of Lead-Based Paint Hazards in Housing." This document provides detailed guidance on identifying lead-based paint and associated hazards in housing, and controlling the hazards safely and efficiently. A significant change made by Title X and the subsequent guidelines was in the working definition of lead-based paint. Lead-based paint hazards now became "any condition that causes exposure to lead from lead-contaminated dust; bare lead-contaminated soil; or lead-based paint that is deteriorated or intact lead-based paint present on surfaces, or impact surfaces that would result in adverse human health effects." U.S. Department of Housing and Urban Development, *The Guidelines for the Evaluation and Control of Lead-Based Paint Hazards in Housing*. Government Printing Office, 1995, p.1-S. Under this definition, intact lead-based paint was not considered a hazard, but should be monitored and controlled. An exception to monitoring plans was still made for Indian and public housing, where the requirement exists to abate if the housing is modernized.

The requirement of Title X for sellers to disclose the existence of lead-based paint in older homes, based on the HUD guidelines, makes it extremely important to have an inexpensive, yet accurate means of testing the existing paint.

Identifying lead-based paint by HUD guidelines can be accomplished by either portable x-ray fluorescence analyzers (XRF) or by laboratory analysis of paint chips. XRFs are expensive to purchase, have radioactive sources, and operators must be trained and licensed. A laboratory analysis is time-consuming, and may also be very costly. Since lead-based paint hazards have gained attention, less costly methods have been developed to identify qualitatively lead-based paint.

Two tests that have been developed include sodium sulfide, and a one-step sodium rhodizonate test. These tests have been put into use in spite of their limitations, which include false positives, false negatives, excessive time required for color change, and difficulties seeing the appropriate color change indicating a positive result.

The "one-step red" sodium rhodizonate test is actually the first step of a test which has been used in the past for the identification of both barium and lead. Use of the "one-step red" test ignores the previously established limitations of the same procedure. In the past, the results provided by the red color in a positive "one-step red" test indicated the presence of both lead and barium. An additional step was required to differentiate between the two, and for the results to be conclusively interpreted as lead.

Recent years have seen an application of a portion of the sodium rhodizonate test to a new area of interest in lead determination. With the concern regarding the presence of lead in paints used in the past, simple testing methods have become advantageous for use in the field. These tests allow the user to make a qualitative analysis of the lead content in a painted surface. The test results can provide the basis for determining the hazards that may arise from the paint removal, or continued exposure to the painted surface. If a field test is not available, the only alternative is instrumental analysis methods, which require laboratory testing or expensive field instruments. Simple testing kits, using the first step in the sodium rhodizonate test, were patented in the early 1990s. These became commercially available, and were accepted for qualitative lead identification in the field. The results of these tests were often used to decide the hazards of the painted surface and the method for paint removal. If the test indicated that the paint was leadbased, considerable expense could be incurred in the removal. Due to variations in the size and conditions of the building, local labor, the market competition, and the type of control selected, cost estimates are difficult; however, in 1991 HUD estimated that control in more than half of the affected housing units could be accomplished for less than $2500 apiece. This cost does not include the initial testing costs, a risk assessment if needed, or the relocation of the occupants during the hazard control.

The interpretations of the results obtained by the new methods in use, however, are in opposition to the interpretations currently accepted by the forensic science community.

In 1995, the American Society for Testing and Materials (ASTM) issued the "Standard Practice for Use of Qualitative Chemical Spot Test Kits for Detection of Lead in Dry Paint Films." The methods used in this standard are the methods used by the commercial kits. Two types of chemical spot tests were evaluated for use in determining lead-based paint. One test uses sodium sulfide, and the other test uses sodium rhodizonate.

The first test uses the reaction of a clear sodium sulfide and lead in situ, or on paint chips. A positive reaction is indicated by a black or gray color. The advantage of this test is that it is easy, relatively inexpensive, and fast. One of the disadvantages is the potential generation of hydrogen sulfide, a toxic gas. Another disadvantage is the fact that the sulfide test is not specific for lead. Several other metal ions react to produce a black color, including iron, nickel, cobalt, copper, mercury and molybdenum. Additionally, a positive test may be difficult to see on a dark surface.

The second test described, and accepted, is the sodium rhodizonate test. The method described by the standard, however, is only the first step of the two-step test that has been used since the 1940s. The standard describes the test as the reaction of the sodium rhodizonate solution and lead to produce a pink or red complex under acid conditions. The ASTM standard further states that one of the advantages of the rhodizonate test is that "Under acid conditions, only lead reacts with the yellow/orange rhodizonate solution to give a pink to red color" and that the reaction with barium produces an orange color (ASTM, 1995a). The ASTM standard does not specify' the pH of the acid conditions, however the method utilizes weak acid at a pH~2.8.

There are several commercially available test kits that use the "one-step-red" sodium rhodizonate test as described in the ASTM method. Some of these include kits marketed under the names LeadCheck, Lead Alert, and EM Lead Test.

The LeadCheck test uses sodium rhodizonate and a weak acid applied directly to the painted surface as disclosed in U.S. Pat. No. 5,330,917 issued to Stone on Aug. 27, 1991. The Manufacturer's Information Sheet included with the test specifies that the appearance of pink, red-pink or red indicates the presence of lead. The Information Sheet states that "Since lead is the only substance that reacts with the dye to give the characteristic pink color, false positive reactions are not likely to occur." The information sheet further identifies barium as the only other substance to react with sodium rhodizonate, however, the result is described as orange instead of pink.

These tests (the "one-step red" tests) fail to explain the inconsistencies of the positive results of these tests, with the interpretation of positive results considered to be conclusive by other researchers. The "One-Step Red" Sodium Rhodizonate Test accepts a red results as specific for lead alone, where other researchers believe that this indicates the presence of both barium and lead.

The same basic premise, using the color change of red to pink to determine the positive presence of lead, has been applied to other media such as glazes and enamels (as disclosed in U.S. Pat. No. 5,010,020 issued to Gould on Apr. 23, 1991) and other surfaces (as disclosed in U.S. Pat. No. 5,039,618 issued to Stone on Aug. 13, 1991). The color change of red to pink in determining lead using rhodizonate dye has also been demonstrated in the application to water, as disclosed in U.S. Pat. No. 5,416,028 issued to Stone on May 16, 1995. These inventions use the rhodizonate dye to react with lead under weak acid conditions.

The primary and critical limitation of the "one-step red" process utilized by currently available test kits appears to be the lack of evidence for the premise that the red color indicates lead, and only lead under the given conditions. This assumption appears to be contrary to previously accepted studies. In the studies reported by the Defense Technical Information Center, the basic premise for the ASTM Spot Test Method, and a product evaluation produced by the OSHA Technical Center, all make the basic assumption that red or pink is conclusive for only lead, and reports that barium produces an orange complex. The OSHA document does, however, specify that "A positive test is evidence of the presence of lead or a positive interference."

The presence of barium in the paint is largely neglected, and considered only as a possible interference. In the past, as well as currently, barium compounds are commonly used in various paint preparations. Barium acetate is used in paint and varnish driers, barium bromate is used as a corrosion inhibitor, and barium chloride is used in pigments. Barium chromate is used as a corrosion inhibitor as well as a pigment in paint. Barium citrate is a stabilizer for latex paints, and barium manganate is used as a paint pigment. Other barium compounds used in paints and as corrosion inhibitors include barium molybdate, barium nitrate, barium potassium chromate, barium sulfate, and barium zirconium silicate.

When the available tests react to form a red complex, which indicates barium or lead, the element present may be only barium. This is a common ingredient of paint, which would result in a false positive. This response could certainly lead to unnecessary abatement measures.

False positives could lead to additional costs for further testing, and/or unnecessary abatement measures, which are extremely expensive. These measures may also delay real estate transactions, and most certainly impose additional problems, paperwork and expense upon the parties involved.

An additional limitation is the accuracy rate of the "one-step red" test. Studies have indicated that the test is not accurate for lead 100% of the time. The study published by the Defense Technical Information Center (DTIC) reported a detection level of 0.38% w/w with a 95% probability of detection. The DTIC also reported an unacceptable level of false positives below 0.4%. These positives may have been due to the presence of barium, resulting in the red barium complex described by other researchers. The testing method used by the OSHA Technical Center appeared to have been limited to only the number of tests possible with each commercially available kit. The kits generally supply materials for one or two tests, so no accuracy rate was reported.

In the "one-step red" test, another limiting factor is the time required to react with chromate, a common ingredient of lead-based paint. The ASTM method specifies that if lead chromate is suspected, a negative result should be examined as long as 24 hours after testing, due to the slow reaction of the chromate with the test kit chemicals. The Manufacturer's Information Sheet from LeadCheck indicates that a positive result may still develop, from an apparent negative sample, anywhere from one hour to overnight. It is certainly possible that a user may interpret the test as a negative, and dispose of the testing materials, when the reaction had not progressed to completion.

These tests, as presently in use, largely ignore the interference of barium, using a test which historically has been used to detect barium. The tests are not completely accurate, may result in false positives when testing for lead, and may require up to 24 hours for completion.

Accordingly, a need exists for a relatively simple "one-step" method of detecting lead in a lead based paint or other media that is accurate, easy to administer, safe, and inexpensive. Preferably, this method should qualitatively identify the presence of lead without interference from other elements or compounds, such as barium, that might lead to a false positive indication. The method should also be highly accurate at relatively low detection levels and provide quick results within minutes of performing the test on a sample.

SUMMARY OF THE INVENTION

A method for qualitatively detecting lead in lead based paint and other media is disclosed using sodium rhodizonate and hydrochloric acid in the presence of lead to form a blue/purple complex. This acidified complex has been accepted as unique to lead and is referred to as the "one-step purple" test.

The major object of the invention is to provide an accurate method for determining the presence of lead in paint and other media.

Another object of the invention is to provide a testing method that is specific for lead, and does not result in false positives due to the presence of other substances.

Another object of the invention is to provide a testing method that gives accurate results in a very short period of time.

Another object is to provide an inexpensive and simple test to be used for qualitatively determining the presence of lead.

The development of a "one-step purple" test fulfills a need for an inexpensive, reliable and rapid field test to be used for the qualitative determination of lead in paint and other media. This test avoids the conflict with the red barium-sodium rhodizonate complex identified in previous methods and safely provides quick and accurate results at relatively low lead concentrations.

The above as well as additional features and advantages of the present invention will become apparent in the following written detailed description.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

DETAILED DESCRIPTION

Figure 1:
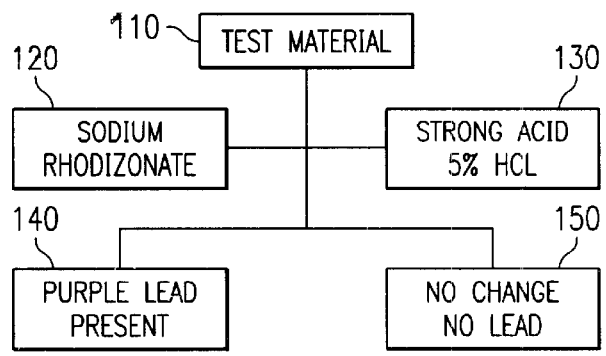
FIG. 1 illustrates a flow chart of the general method of the invention.

FIG. 1 shows a flow chart demonstrating the overall method of the invention. A test material 110 is first identified. This test material 110 could be a chip of paint suspected of containing lead or some other media (emulsion, slurry, liquid mixture, etc . . . ) which requires testing to determine the presence of lead or a lead based compound. Sodium rhodizonate 120 and hydrochloric acid 130 are then applied to the test material 130 simultaneously or within a short period of time (thus a "one-step" test is performed). If after a short period of time, less than one minute, the tested sample exhibits a purple tint 140 then lead or a lead-based compound has been detected. However, if there is no change 150 exhibited by the tested sample, then there is no lead or lead based compound in the material.

One embodiment of the invention's method consists of applying hydrochloric acid to a cotton swab, scrubbing a painted surface in an area approximately 1 square centimeter in size, and applying one drop of sodium rhodizonate solution to the swab. Three drops of hydrochloric acid are considered optimum. Less than three drops does not adequately break down the paint matrix. The duration of scrubbing depends upon the paint deposit upon the swab. When paint is visible upon the swab, the scrubbing is stopped. If no paint is visible, the board is scrubbed for 5 seconds. One drop of sodium rhodizonate is then applied directly to the cotton swab. The presence of lead is indicated by a color change to purple/blue. The color change is detectable within one minute.

The solution of sodium rhodizonate prepared to the color of strong tea contributes to the best results. The hydrochloric acid recommended is a 5% solution, as this is the lowest concentration that gives accurate results. The sodium rhodizonate dye as used herein, is formed from the addition of distilled or deionized water, to a salt of rhodizonic acid. The salts include but are not limited to sodium salt, disodium salt, and potassium salts.

Using the above disclosed method, the presence of lead has been detected in the latex-based paint in the full range of variables. Tests using this method were positive in detecting from 40% to 0.016% lead acetate concentrations (w/w), with various solutions of sodium rhodizonate and various concentrations of hydrochloric acid. In oil-based paints, positive results were achieved from 40% to 0.016% lead concentrations, again using various combinations of hydrochloric acid with a 970 ppb sodium rhodizonate solution. The combination of 50% hydrochloric acid with 388 ppb solution resulted in a trace of purple/blue color, however the trace was not sufficient to be considered conclusive. The limits of detection may vary when media other than paint is tested.

In another embodiment of the invention, a cotton swab is impregnated with 5% hydrochloric acid. The cotton swab is rubbed on the surface to be tested. One drop of sodium rhodizonate solution is applied to the cotton swab. A color change of purple/blue indicates the presence of lead.

Figure 2:
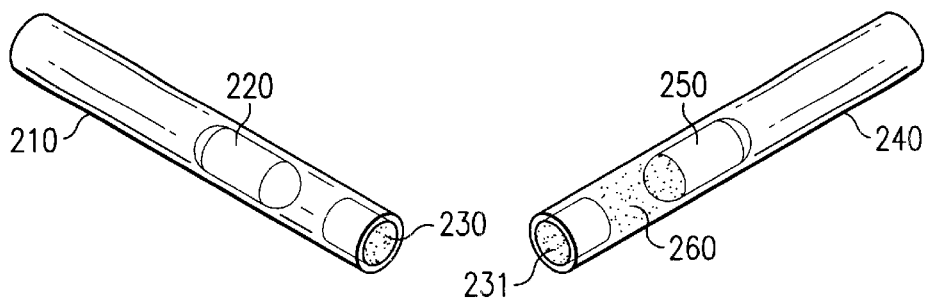
FIG. 2 illustrates an embodiment of the invention consisting of two flexible or crushable cylinders, each containing a breakable ampoule, and absorbent material on one end.

FIG. 2 illustrates another embodiment of the invention, in which a plastic cylinder or cartridge 210 is used, with an ampoule 220 inside containing dilute hydrochloric acid. One end of the plastic cylinder contains an absorbent material 230 such as packed cotton with the other end being sealed. The user squeezes the flexible cylinder 210, cracking or breaking the ampoule, thus releasing the hydrochloric acid into the absorbent material 230. The absorbent material 230 is then rubbed upon the surface to be tested. A second cylinder or cartridge 240 contains distilled or deionized water in the inner ampoule 250 and sodium rhodizonate (rhodizonic acid, disodium or dipotassium salt) 260 in the plastic cylinder 240. Breaking the inner ampoule 250 releases the water, forming the fresh sodium rhodizonate solution, impregnating the absorbent material 231 found at one end of the plastic cylinder 240. Touching the ends of the cylinders 210, 240 together such that the two now moist areas comprising absorbent material 230, 231 come into contact will result in a blue/purple color change on either or both absorbent tips in the presence of lead.

Figure 3:
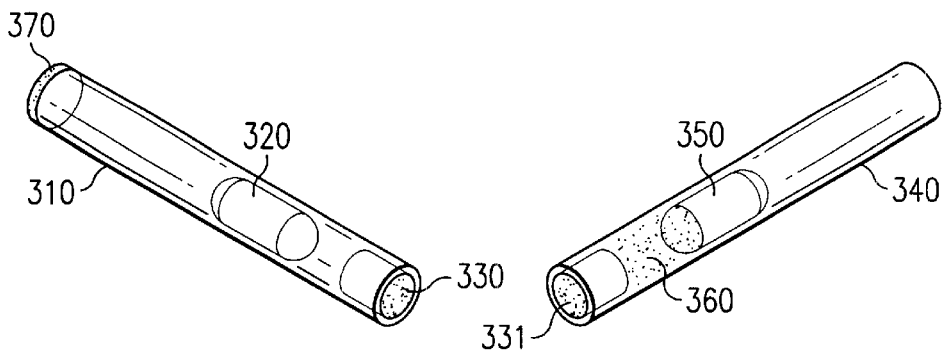
FIG. 3 illustrates an embodiment of the invention consisting of two flexible or crushable cylinders, each containing a breakable ampoule, and absorbent material on one end, while one cylinder is additionally covered with abrasive material, such as sandpaper, at the opposite end of the absorbent material.

In another embodiment of the invention illustrated in FIG. 3, a plastic cylinder is used, with an inner, breakable ampoule 320 containing the dilute hydrochloric acid. One end of the plastic cylinder 310 is packed with cotton or absorbent material 330. The opposite end of the cylinder 310 is covered with an abrasive material 370. The abrasive material 370 is used to scratch the painted surface to increase the ease of dissolution of the paint. The sodium rhodizonate solution is then applied using the second cylinder 340 (as previously described) comprising one end containing absorbent material 351, an inner ampoule 350 containing water, and sodium rhodizonate 360. The color change of blue/purple indicates the presence of lead.

Figure 4:
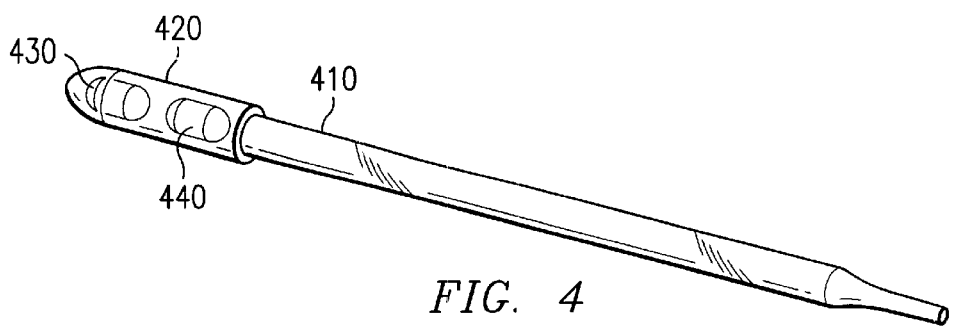
FIG. 4 illustrates an embodiment of the invention consisting of a dropper, with a flexible or crushable end containing two ampoules.

An additional embodiment illustrated in FIG. 4, uses an alternative method of application for the sodium rhodizonate. A delivery system comprising a dropper 410 is used. The top part of the dropper 420 is a flexible material, containing an ampoule 430 of distilled or deionized water. Also contained in the top portion 420 is sodium rhodizonate powder 440. The powder 440 and ampoule 430 are contained in a permeable bag (not shown), in the squeezable end 420 of the dropper. The ampoule 430 in the flexible end 420 of the dropper is broken, and the flexible portion 420 facilitates delivery of one drop of sodium rhodizonate solution to the tip of an acidified swab (not shown), which has been rubbed upon the test surface. In this embodiment of the invention, multiple acid swabs can be packaged together, with a single dropper of sodium rhodizonate. This allows multiple testing of surfaces by applying additional drops of sodium rhodizonate from one dropper to more than one acid swab.

In another embodiment of the invention, water can be tested for the presence of lead. Several drops of test water are dropped on an absorbent paper media. The water is dried through natural evaporation, or by application of heat. One drop of dilute hydrochloric acid is applied to the dried water spot. Sodium rhodizonate solution is the added, drop by drop to the moistened spot. If lead is present, the spot will turn blue/purple. If no lead is present the spot will remain clear, and turn to the color of the sodium rhodizonate solution with the continued addition of the solution.

In another embodiment of the invention, a small amount of solid material can be dissolved or placed in a several drops of dilute hydrochloric acid. Sodium rhodizonate solution is added slowly until the acid turns to the color of the sodium rhodizonate. If lead is present, the acid will exhibit a blue/purple color before the solutions turns to the yellow/brown color of the sodium rhodizonate solution.

In an additional embodiment of the invention, the reagent kit is supplemented with a printed color chart showing the expected colors indicated by the positive presence of lead. Research with lead-based paint has shown that the approximate concentration of lead is related to the intensity of the color reaction. An additional embodiment includes a progressive color chart relating the lead concentration to the color on the chart.

In another embodiment, one drop of dilute hydrochloric acid is applied directly to the surface of the material to be tested. One drop of sodium rhodizonate is then applied to the same spot, and the spot is observed for a color change. A color change of blue/purple indicates the presence of lead.

In an additional embodiment, the surface to be tested is abraded before the application of the dilute hydrochloric acid. The sodium rhodizonate solution is then applied, and the area is observed for a color change.

This "one-step purple" test is a substantial improvement in the art due to its accuracy, imperviousness to interference and false positive indications, and relatively fast reaction times. In short, this invention is safe, effective, and inexpensive, thus providing a superior testing means over those test methods presently enjoying considerable market success.

Additional reference information regarding various embodiments of the invention and descriptive detail can be found in Applicant's thesis on the invention, copyright 1998, attached to the provisional filing of this application and which is available to the public at the University of Oklahoma Library in Norman, Okla.

While the invention has been particularly shown and described with reference to preferred embodiments and to illustrate the principles, it will be understood by those skilled in the art that various changes and modifications in form and detail may be made therein without departing from the spirit and scope of the invention.

What is claimed is:

1. A method of detecting lead in a media which comprises the steps of:

(a) exposing the media to a hydrochloric acid;

(b) exposing the media to sodium rhidozonate; and, (c) monitoring the media for a visible color change.

2. The method of claim 1 wherein the color change of step (c) is a purple to blue tint.

3. The method of claim 1 wherein the rhodizonate is formed from a rhodizonic acid salt and water.

4. The method of claim 1 wherein the rhodizonate is formed from rhodizonic acid, disodium salt, and water.

5. The method of claim 1 wherein the rhodizonate concentration appears as a yellow/brown color.

6. The method of claim 1 wherein the dilute hydrochloric acid comprises a concentration of approximately 5%. volume to volume.

7. The method of claim 1 further comprising the steps of:

(d) comparing the color change to a color chart.

8. The method of claim 7 wherein the color chart contains a range of colors indicating the positive or negative detection of lead.

9. The method of claim 7 wherein the color chart contains a range of colors in which the positive colors are correlated to a detected lead concentration.

10. A method of detecting lead in a media which comprises the steps of:

(a) abrading the media;

(b) exposing the media to a hydrochloric acid;

(c) exposing the media to a sodium rhidozonate; and, (d) monitoring the media for a visible color change.

11. The method of claim 10 wherein the color change of step (d) is a purple to blue tint.

12. The method of claim 10 wherein the rhodizonate is formed from a rhodizonic acid salt and water.

13. The method of claim 10 wherein the rhodizonate is formed from rhodizonic acid, disodium salt, and distilled water.

14. The method of claim 10 wherein the sodium rhodizonate concentration appears as a yellow/brown color.

15. The method of claim 10 wherein the dilute hydrochloric acid comprises a concentration of approximately 5%. volume to volume.

16. The method of claim 10 wherein the color change of step (d) is further compared to a color chart.

17. The method of claim 16 wherein the color chart contains a range of colors indicating the positive or negative detection of lead.

18. The method of claim 16 wherein the color chart contains a range of colors in which the positive colors are correlated to a detected lead concentration.

* * * * *